United States Patent
Uehara

(10) Patent No.: US 11,406,341 B2
(45) Date of Patent: Aug. 9, 2022

(54) RADIOGRAPHY CONTROL APPARATUS, RADIOGRAPHIC IMAGING APPARATUS, AND RADIOGRAPHIC IMAGING SYSTEM

(71) Applicant: KONICA MINOLTA, INC., Tokyo (JP)

(72) Inventor: Takahisa Uehara, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/584,926

(22) Filed: Sep. 26, 2019

(65) Prior Publication Data

US 2020/0100754 A1    Apr. 2, 2020

(30) Foreign Application Priority Data

Sep. 27, 2018 (JP) .............................. JP2018-181247

(51) Int. Cl.
*A61B 6/00* (2006.01)
*H04N 5/32* (2006.01)

(52) U.S. Cl.
CPC ............ *A61B 6/5211* (2013.01); *A61B 6/542* (2013.01); *H04N 5/32* (2013.01)

(58) Field of Classification Search
CPC ........... H04N 5/32; A61B 6/00; A61B 6/5211; A61B 6/542; A61B 6/5264; A61B 6/563
See application file for complete search history.

(56) References Cited

U.S. PATENT DOCUMENTS

| 7,340,034 B2 | 3/2008 | Hayashida et al. |
| 8,611,500 B2 | 12/2013 | Tsuchiya |
| 8,948,342 B2 | 2/2015 | Tsuchiya |
| 9,322,928 B2 | 4/2016 | Iwakiri et al. |
| 10,390,783 B2 * | 8/2019 | Hawver .................. A61B 6/585 |
| 10,413,269 B2 * | 9/2019 | Nagano .................. A61B 6/06 |
| 2009/0129679 A1 | 5/2009 | Miyamoto |
| 2018/0055473 A1 * | 3/2018 | Torii ...................... A61B 6/542 |
| 2018/0110491 A1 | 4/2018 | Ishida et al. |

FOREIGN PATENT DOCUMENTS

| JP | 2009119133 A | 6/2009 |
| JP | 4708944 B2 | 6/2011 |
| JP | 2013172782 A | 9/2013 |
| JP | 2014147844 A | 8/2014 |
| JP | 5597055 B2 | 10/2014 |
| JP | 2017018705 A | 1/2017 |
| JP | 2018068400 A | 5/2018 |
| WO | 2013038896 A1 | 3/2013 |

OTHER PUBLICATIONS

Japanese Office Action (and English language translation thereof) dated Jan. 4, 2022, issued in counterpart Japanese Application No. 2018-181247.

* cited by examiner

*Primary Examiner* — Jurie Yun

(74) *Attorney, Agent, or Firm* — Holtz, Holtz & Volek PC

(57) ABSTRACT

A console 3 included in a radiographic imaging system 100 includes a hardware processor that acquires a plurality of radiographs from a radiographic imaging apparatus 2 that repeatedly generates radiographs in a predetermined cycle, determines whether there is an anomaly that occurred during radiography of the acquired radiographs, and on determining that there is an anomaly, performs a predetermined anomaly operation.

21 Claims, 7 Drawing Sheets

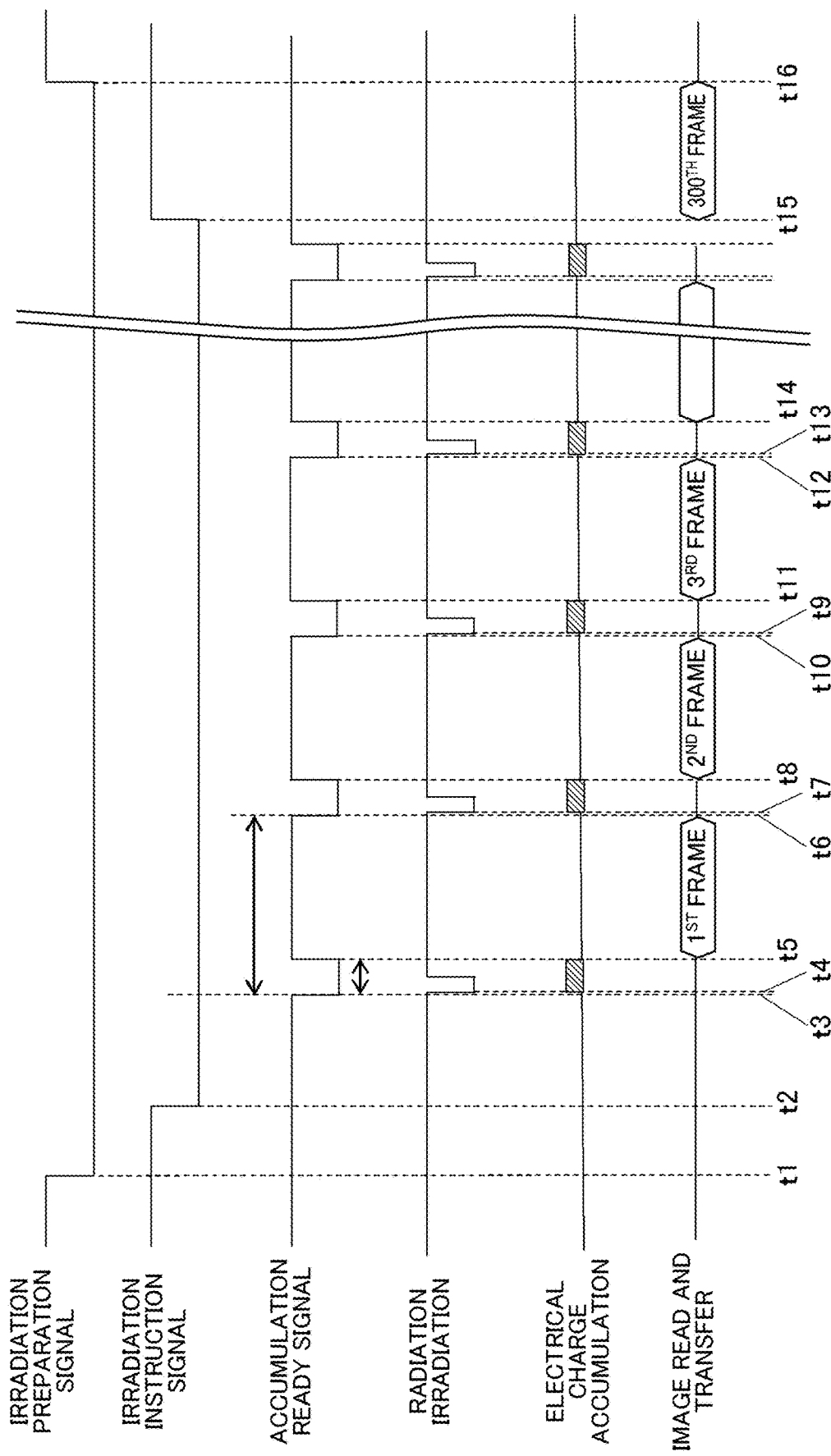

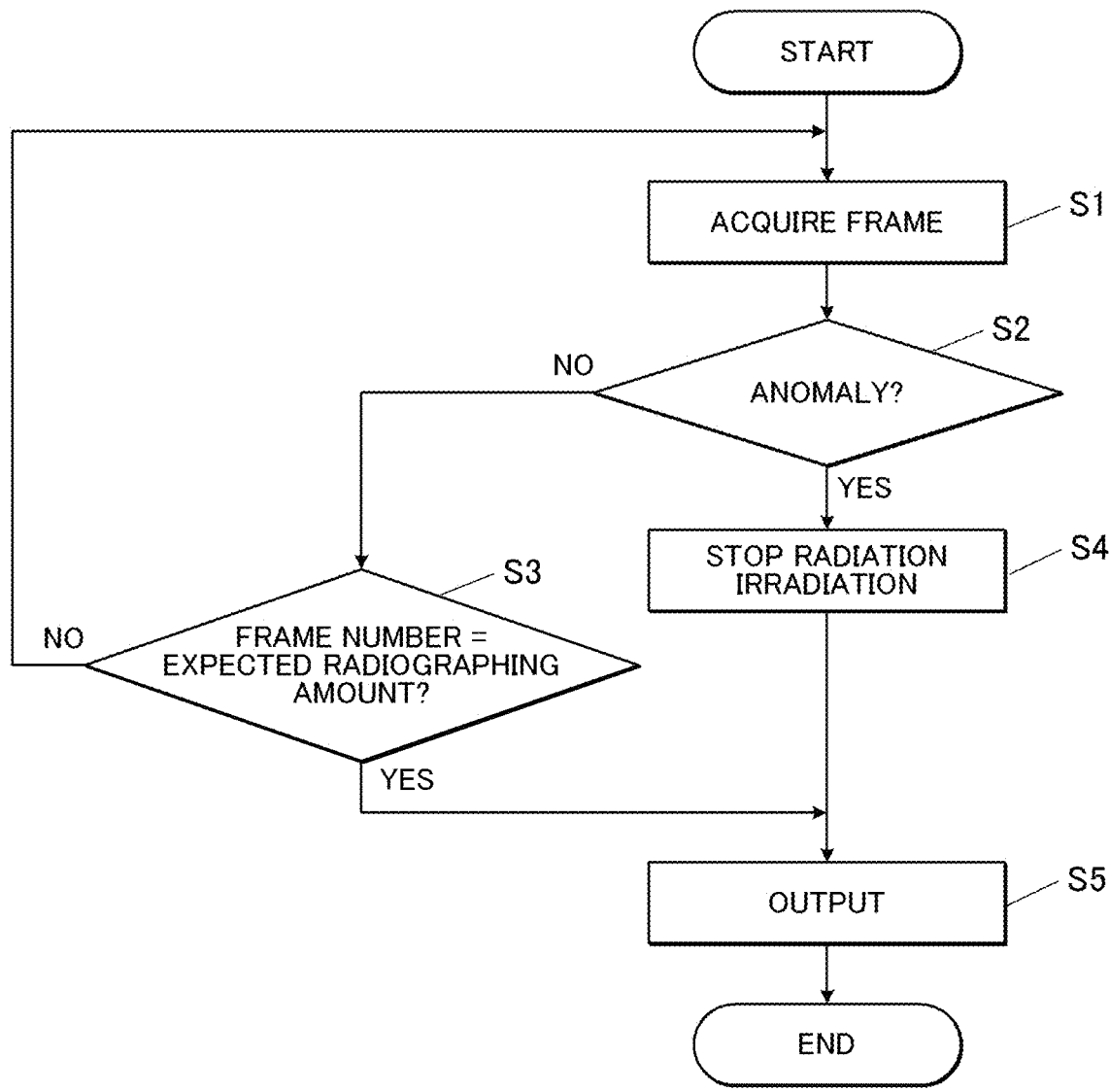

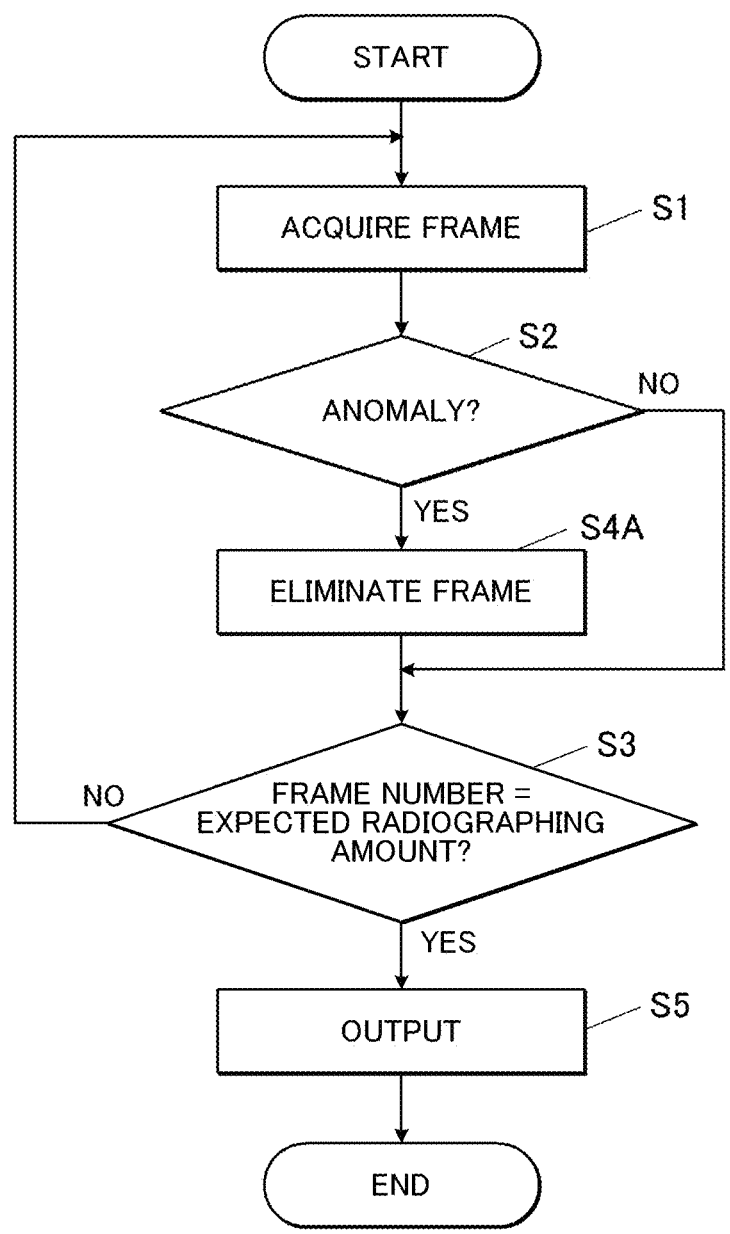

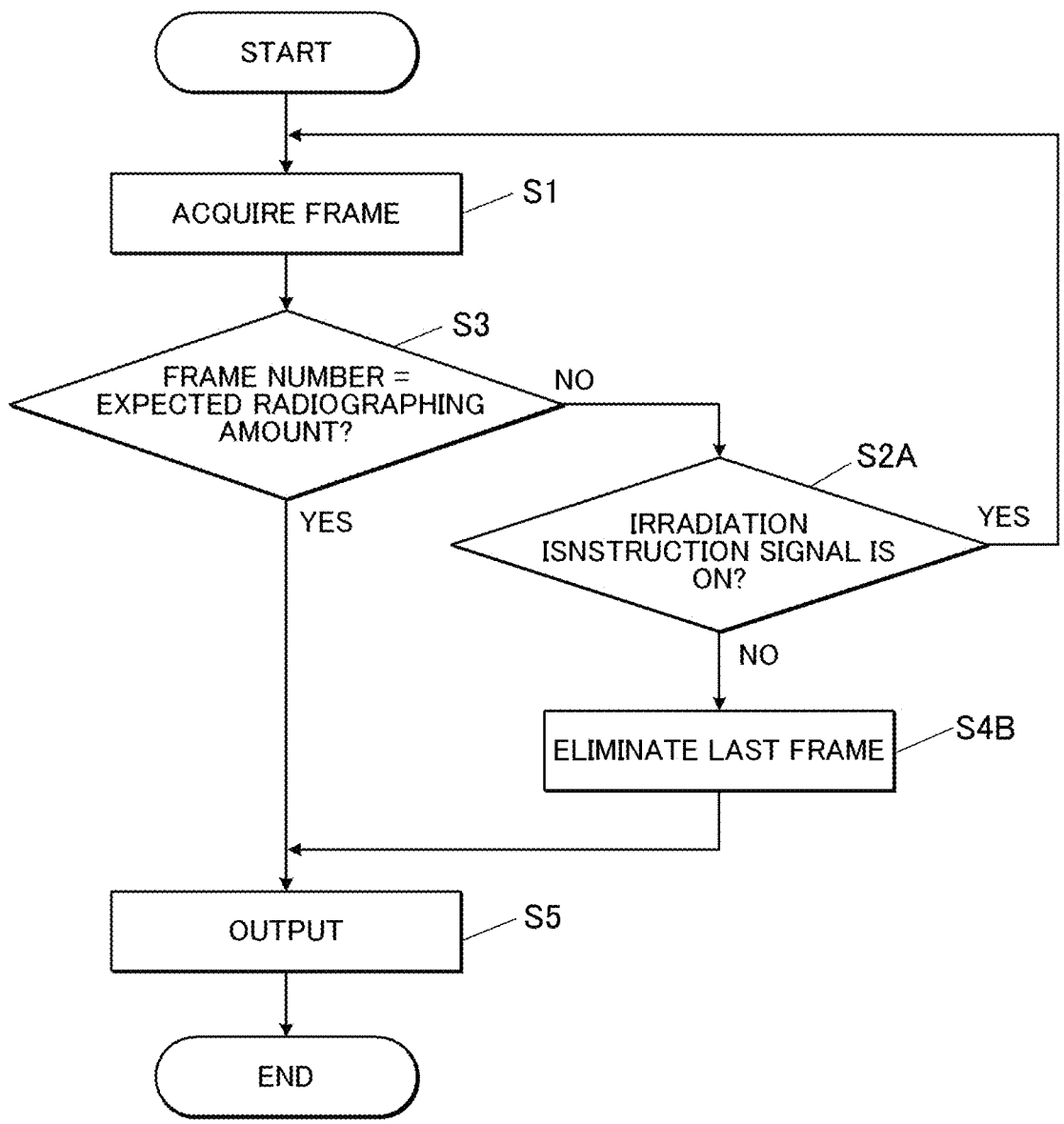

RADIOGRAPHY CONTROL APPARATUS, RADIOGRAPHIC IMAGING APPARATUS, AND RADIOGRAPHIC IMAGING SYSTEM

BACKGROUND

Technological Field

The present invention relates to a radiography control apparatus, a radiographic imaging apparatus, and a radiographic imaging system.

Description of the Related Art

Among radiographic imaging systems including a radiation generating apparatus that generates radiation and a radiographic imaging apparatus that generates a radiograph corresponding to the received dose of radiation, some systems have been recently developed that are capable of, in addition to still-image radiography, dynamic-image radiography (serial radiography) in which irradiation of radiation and generation of a radiograph are repeated at high speed. The dynamic image obtained from dynamic-image radiography is transferred to an analytical diagnosis workstation to be used for analysis of respiration, blood flow, and the like (see JP 2014-147844A, JP 2018-068400A).

In order to perform dynamic-image radiography, the timing when the radiation generating apparatus generates radiation and the timing when the radiographic imaging apparatus generates a radiograph need to be synchronized. As a synchronization method, there has been a method of exchanging control signals between the radiation generating apparatus and the radiographic imaging apparatus, for example (see JP 2017-018705A).

In addition, in dynamic-image radiography, in some cases, the input timing of a control signal instructing the radiation generating apparatus to irradiate radiation may not match the timing when the radiation generating apparatus starts irradiating radiation in response to the input of the control signal (delayed radiation irradiation). This timing difference sometimes affects the quality of the dynamic image.

In view of such a problem, a recently proposed technique includes: acquiring an output timing of a control signal to the radiation generating apparatus to instruct irradiation of radiation based on a signal from the radiation generating apparatus; acquiring an operation timing at which the radiation generating apparatus generates radiation based on an output value read by the radiographic imaging apparatus and the time required for reading; and obtaining a delay time of the operation of the radiation generating apparatus based on the acquired output timing and operation timing to control (e.g., hasten output timing of control signal) the radiographic imaging apparatus based on the obtained delay time (see JP 5597055B).

In addition to the delayed radiation irradiation described in the aforementioned JP 5597055B, conceivable problems during dynamic-image radiography include a problem of irradiation failure or low-dose (lower than dose specified before radiography) exposure due to performance of the radiation generating apparatus or radiographic imaging apparatus or the coordination scheme between the two.

Incidentally, such problems of irradiation failure and low-dose may occur when the user accidentally releases an exposure switch during operation.

When an unexposed image generated by irradiation failure or a less exposed image generated by low-dose irradiation is included as a frame forming a dynamic image, analysis accuracy deteriorates, which may require the dynamic-image radiographing to be performed again under the same conditions.

Additionally, in dynamic-image radiography, the radiographing time is longer (such as over ten seconds) than still-image radiography. Hence, in dynamic-image radiography, the subject is sometimes unable to keep the still posture and may move (body movement may occur) during radiography.

After radiographing the dynamic image, the user plays back the dynamic image to check whether there is an anomalous image resulting from the above problems. If an anomalous image is found, the dynamic-image radiographing needs to be performed again under the same conditions.

When radiographing is performed again, the subject is needlessly exposed for the amount of radiography of another dynamic-image.

SUMMARY

In view of the foregoing, an objective of the present invention is to suppress the exposure amount of a subject upon occurrence of an anomaly as compared to conventional techniques, in dynamic-image radiography in which irradiation of radiation and radiograph generation are repeated at high speed.

To achieve at least one of the abovementioned objects, according to a first aspect of the present invention, a radiography control apparatus reflecting one aspect of the present invention comprises a hardware processor that
acquires a plurality of radiographs from a radiographic imaging apparatus that repeatedly generates radiographs in a predetermined cycle,
determines whether there is an anomaly that occurred during radiography of the acquired radiographs, and
on determining that there is an anomaly, performs a predetermined anomaly operation.

According to a second aspect of the present invention, a radiographic imaging apparatus reflecting one aspect of the present invention comprises a radiation detector in which a plurality of radiation detecting elements that generate electrical charge corresponding to a received dose of radiation are arranged in a two-dimensional manner, and
a hardware processor that
alternates accumulation of electrical charge in the radiation detecting element and reading of the electrical charge accumulated in the radiation detecting element repeatedly in a predetermined cycle,
determines whether an anomaly occurred when the read electrical charge was accumulated in the radiation detecting element, and
on determining that there is an anomaly, performs a predetermined anomaly operation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 5 is a timing chart showing operations of the radiation generating apparatus and the radiographic imaging apparatus when dynamic-image radiography is performed using the radiographic imaging system of FIG. 1.

FIG. 6 is a flowchart showing an operation of the console when dynamic-image radiography is performed using the radiographic imaging system of the first embodiment.

FIG. 7 is a flowchart showing an operation of a console when dynamic-image radiography is performed using a radiographic imaging system of a second embodiment.

FIG. 8 is a flowchart showing an operation of a console when dynamic-image radiography is performed using a radiographic imaging system of a third embodiment.

DETAILED DESCRIPTION OF EMBODIMENTS

Hereinafter, one or more embodiments of the present invention will be described with reference to the drawings. However, the scope of the invention is not limited to the disclosed embodiments.

<First Embodiment>

Hereinafter, a first embodiment of the present invention will be described in detail with reference to FIGS. 1 to 6.

[Radiographic Imaging System]

Figure 1:
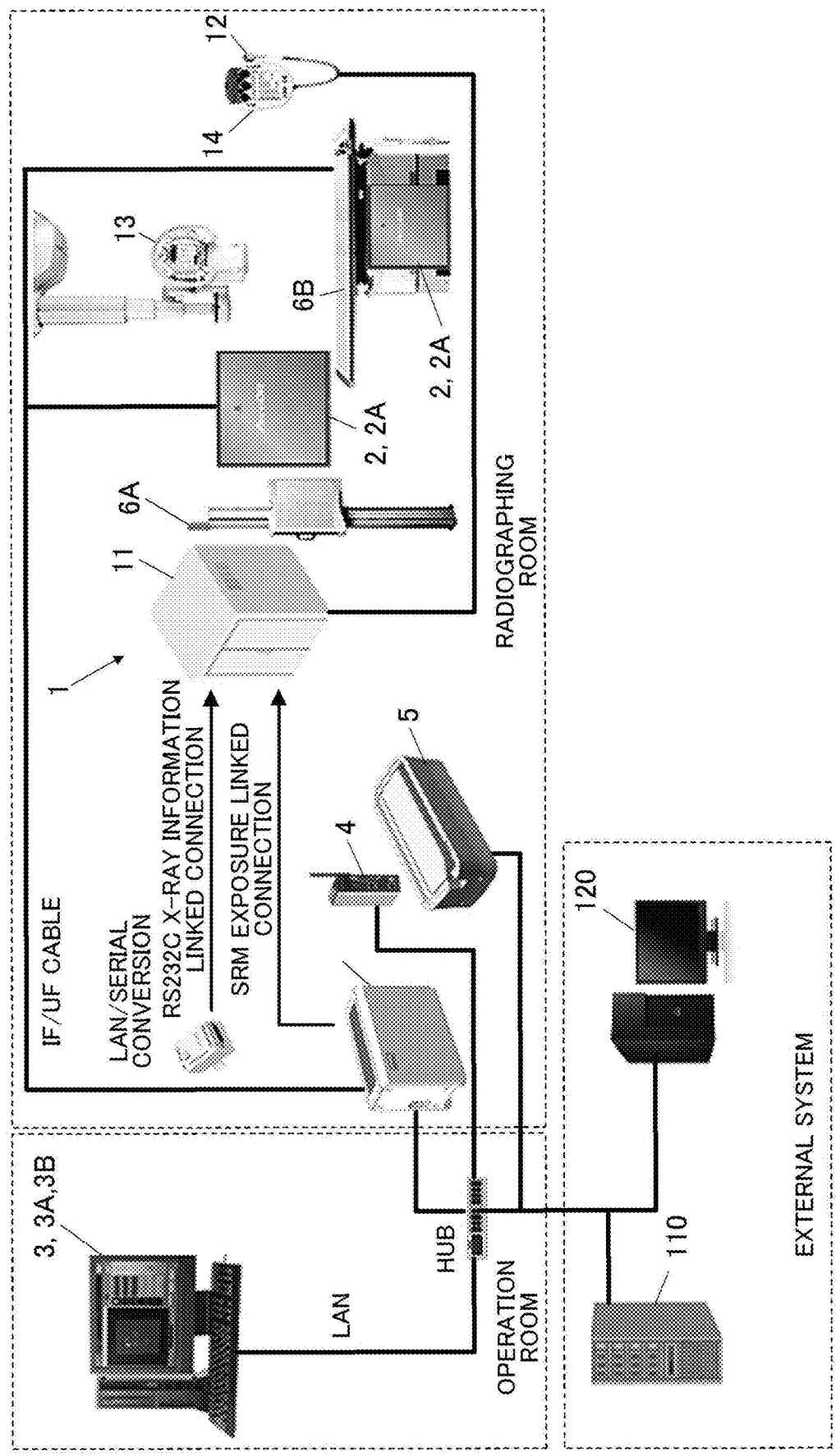
FIG. 1 is a block diagram showing a radiographic imaging system of a first embodiment (second to fourth embodiments) of the present invention.

First, a configuration of a radiographic imaging system of the embodiment will be described. FIG. 1 is a block diagram showing a configuration of a radiographic imaging system 100. Note that the bracketed reference numerals in FIG. 1 are those of later-mentioned second to fourth embodiments.

As shown in FIG. 1, the radiographic imaging system (hereinafter referred to as system 100) of the embodiment includes a radiation generating apparatus (hereinafter referred to as generating apparatus 1), a radiographic imaging apparatus (hereinafter referred to as radiographing apparatus 2), and a console 3.

In addition, the system 100 is capable of communicating with a picture archiving and communication system (hereinafter referred to as PACS 110), an analytical diagnosis workstation (WS) 120, and the like through a communication network.

Note that the system 100 may be capable of communicating with an unillustrated hospital information system (hereinafter referred to as HIS), radiology information system (hereinafter referred to as RIS), general purpose client terminal, or the like.

Moreover, other than the above components, the system 100 may include an access point 4 for wireless communication, a cradle 5 for charging the radiographing apparatus 2 and transmitting/receiving data, and at least one of a radiography base 6A for standing radiography and a radiography base 6B for lying radiography that support the radiographing apparatus 2.

In addition, while FIG. 1 exemplifies a case where the system 100 is installed in a facility (radiographing room, operation room), the system 100 may be built in a visiting car or the like to be movable.

The generating apparatus 1 includes a generator 11, an exposure switch 12, and a radiation source (vessel) 13, and is capable of irradiating the radiographing apparatus 2 with radiation.

Additionally, the generating apparatus 1 is capable of communicating with the radiographing apparatus 2 and the console 3 through wired or wireless communication.

Note that other than the above components, the generating apparatus 1 may include a radiation generation controller 14, an interface unit 15, and the like.

Figure 2:
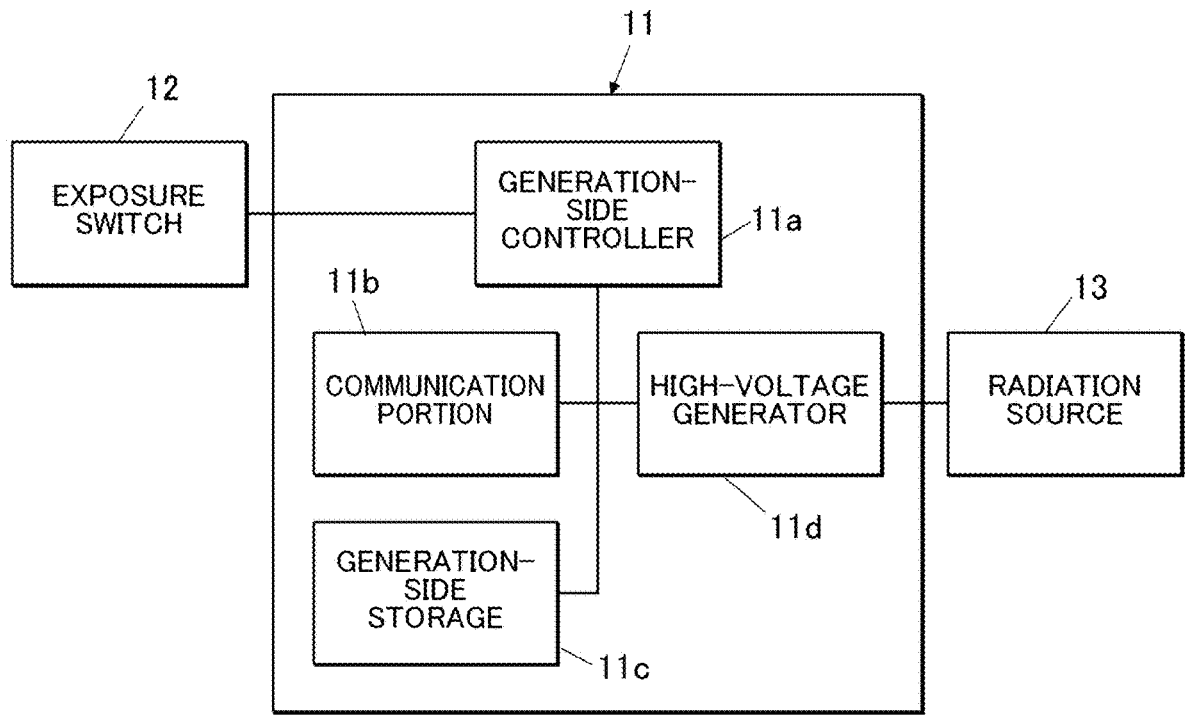
FIG. 2 is a block diagram showing a configuration of a radiation generating apparatus included in the radiographic imaging system of FIG. 1.

Moreover, while FIG. 1 exemplifies a case where the exposure switch 12 is connected to the radiation generation controller 14, the exposure switch 12 may be directly connected to the generator 11 (FIG. 2).

Additionally, the radiation generation controller 14 may be integrated with the console 3.

Details of the generating apparatus 1 will be described later.

The radiographing apparatus 2 is capable of generating a radiograph corresponding to the received dose of radiation.

Additionally, the radiographing apparatus 2 is capable of communicating with the console 3 through wired or wireless communication.

Note that while FIG. 1 exemplifies the radiographing apparatus 2 as a panel-shaped portable type (cassette type), the radiographing apparatus 2 may be fixed in a facility or to the radiography base 6A, 6B, or may be in a form other than a panel.

Details of the radiographing apparatus 2 will be described later.

The console 3 serves as a radiography control apparatus of the present invention, and is configured of a PC, a mobile terminal, or a dedicated apparatus.

Additionally, the console 3 is capable of communicating with the generating apparatus 1, the radiographing apparatus 2, and the like through wired or wireless communication.

Note that the radiography control apparatus may be configured as an apparatus separate from the console instead of assigning the function of a radiography control apparatus to the console 3.

Details of the console 3 will be described later.

[Radiation Generating Apparatus]

Next, details of the generating apparatus 1 included in the system 100 will be described. FIG. 2 is a block diagram showing a configuration of the generating apparatus 1.

As shown in FIGS. 1 and 2, the generating apparatus 1 includes the generator 11, the exposure switch 12, and the radiation source 13.

The generator 11 includes a generation-side controller 11$a$, a communication portion 11$b$, a generation-side storage 11$c$, and a high-voltage generator 11$d$.

The generation-side controller 11$a$ includes a central processing unit (CPU), a random access memory (RAM), and the like. The CPU reads various programs stored in the generation-side storage 11$c$ based on a control signal or the like from another apparatus (console 3 or the like) to deploy the programs in the RAM, executes various processing according to the deployed programs, and has centralized control over operations of parts of the generating apparatus 1.

The communication portion 11$b$ is configured of a network interface or the like.

In addition, the communication portion 11$b$ is capable of exchanging various control signals and various types of data and the like including radiograph data with other apparatuses (radiographing apparatus 2 and console 3).

The generation-side storage 11c is configured of a hard disk drive (HDD), a semiconductor memory, and the like.

Additionally, the generation-side storage 11c stores various processing programs and parameters, files, and the like necessary for execution of the processing programs.

The high-voltage generator 11d applies, to the radiation source 13, a voltage corresponding to a set radiographing condition (e.g., radiography method such as still-image radiography and dynamic-image radiography, radiographing target portion, condition regarding subject such as physique, tube voltage and tube current, irradiation time, current-time product (mAs value), frame rate (fps), and condition regarding irradiation of radiation such as expected radiographing amount or scheduled radiographing period).

The exposure switch 12 can be operated in two steps.

When a voltage is applied from the high-voltage generator 11d, the radiation source 13 generates radiation (such as X-ray) of a dose corresponding to the applied voltage.

The generation-side controller 11a of the generator 11 configured in the above manner turns ON an irradiation preparation (Prepare) signal output to the radiographing apparatus 2 through the communication portion 11b when the first step of the exposure switch 12 is operated, and turns OFF the irradiation preparation signal when the operation of the first step is cancelled.

Additionally, the generation-side controller 11a turns ON an irradiation instruction (Exposure) signal output to the radiographing apparatus 2 through the communication portion 11b when the second step of the exposure switch is operated, and turns OFF an irradiation instruction signal when the operation of the second step is cancelled.

Moreover, the generation-side controller 11a causes the high-voltage generator 11d to apply a predetermined voltage to the radiation source 13 when an accumulation ready (Ready) signal input from the radiographing apparatus 2 through the communication portion 11b is turned ON while the irradiation instruction signal is ON. As a result, the radiation source 13 generates a predetermined dose of radiation.

In the case of still-image radiography, the accumulation ready signal is turned ON only once while the irradiation instruction signal is ON. Meanwhile, in the case of dynamic-image radiography, ON/OFF of the accumulation ready signal is repeated in a predetermined cycle (e.g., 15 fps) while the irradiation instruction signal is ON. Accordingly, application of a voltage by the high-voltage generator 11d (generation of radiation from radiation source 13) is also repeated in a predetermined cycle.

[Radiographic Imaging Apparatus]

Figure 3:
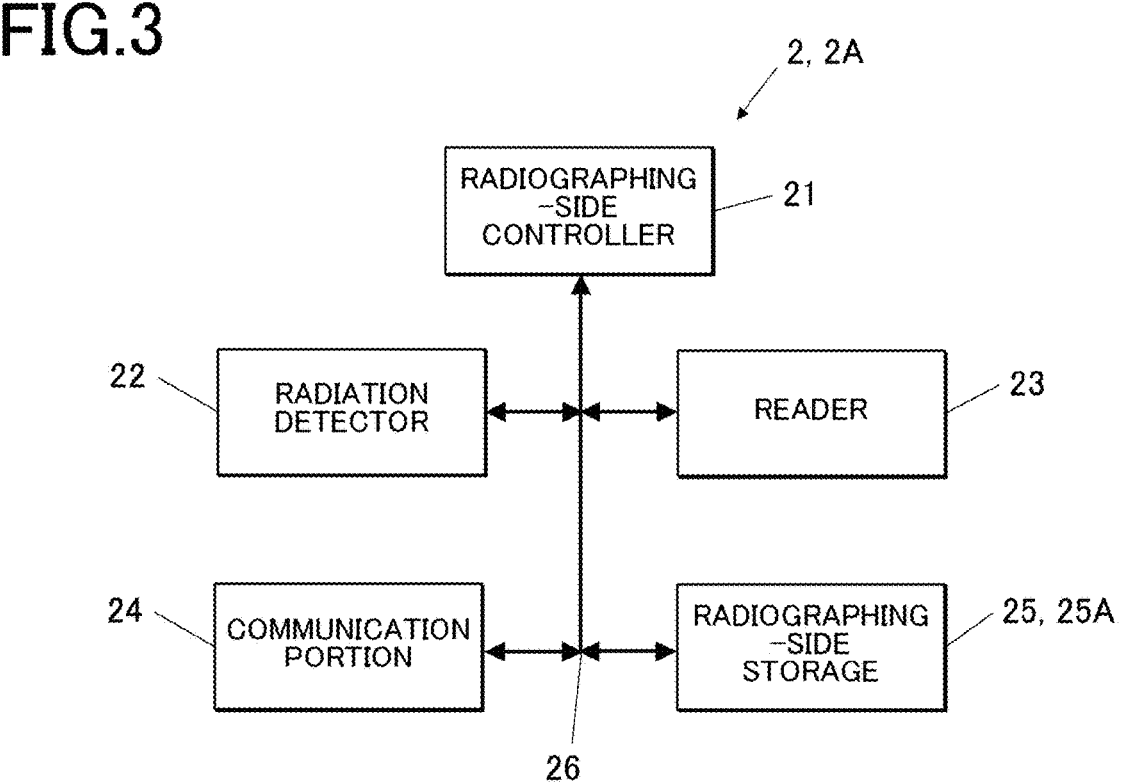
FIG. 3 is a block diagram showing a configuration of a radiographic imaging apparatus included in the radiographic imaging system of FIG. 1.

Next, details of the radiographing apparatus 2 included in the above system 100 will be described. FIG. 3 is a block diagram showing a configuration of the radiographing apparatus 2. Note that the bracketed reference numerals in FIG. 3 are those of the later-mentioned fourth embodiment.

As shown in FIG. 3, the radiographing apparatus 2 includes a radiographing-side controller 21, a radiation detector 22, a reader 23, a communication portion 24, a radiographing-side storage 25, and a bus 26 that connects the parts of the radiographing apparatus 2.

The radiographing-side controller 21 includes a CPU, a RAM, and the like. The CPU reads various programs stored in the radiographing-side storage 25 based on a control signal or the like from another apparatus (console 3 or the like) to deploy the programs in the RAM, executes various processing according to the deployed programs, and has centralized control over operations of parts of the radiographing apparatus 2.

The radiation detector 22 has a radiation detecting element that generates electrical charge corresponding to the received dose of radiation, and a substrate on which a plurality of switching elements for switching ON/OFF between the radiation detecting element and the reader 23 are arranged in a two-dimensional manner (in a matrix).

Note that the radiation detector 22 may have a built-in scintillator, and convert the received radiation into light having another wavelength such as visible light with the scintillator to generate electrical charge corresponding to the converted light (so-called indirect type), or may generate electrical charge directly from the radiation without having a scintillator or the like interposed therebetween (so-called direct type).

The reader 23 is capable of reading the amount of electrical charge emitted from each radiation detecting element as a signal value and generating a radiograph based on the obtained a plurality of signal values.

The communication portion 24 is configured of a network interface or the like.

In addition, the communication portion 24 is capable of exchanging various control signals and various types of data including radiograph data with other apparatuses (generating apparatus 1 and console 3).

The radiographing-side storage 25 is configured of a nonvolatile semiconductor memory, a hard disk, and the like.

Additionally, the radiographing-side storage 25 stores various programs executed by the radiographing-side controller 21 and parameters and the like necessary for execution of processing by the programs.

Moreover, the radiographing-side storage 25 can store various types of data including image data generated by the reader 23.

The radiographing-side controller 21 of the radiographing apparatus 2 configured in the above manner turns ON the accumulation ready signal in response to turning ON of the irradiation instruction signal input from the generating apparatus 1 through the communication portion 24, and turns OFF the accumulation ready signal after passage of a predetermined time period.

In the case of still-image radiography, ON/OFF of the accumulation ready signal is performed only once while the irradiation instruction signal input from the generating apparatus 1 is ON. Meanwhile, in the case of dynamic-image radiography, ON/OFF of the accumulation ready signal is repeated in a predetermined cycle (e.g., 15 times per second) while the irradiation instruction signal is ON.

Additionally, the radiographing-side controller 21 stops the operation of turning ON the accumulation ready signal (keeps accumulation ready signal OFF) in response to turning OFF of the irradiation instruction signal.

Moreover, the radiographing-side controller 21 turns OFF each switching element of the radiation detector 22 to make each radiation detecting element ready to accumulate electrical charge every time the accumulation ready signal is turned ON, and turns ON each switching element of the radiation detector 22 to emit the electrical charge accumulated in the radiation detecting element to the reader 23 every time the accumulation ready signal is turned OFF.

In the case of dynamic-image radiography, the radiographing-side controller 21 repeats ON/OFF of the accumulation ready signal in a predetermined cycle, and therefore also repeats accumulation of electrical charge in the radiation detecting element and reading of the electrical charge accumulated in the radiation detecting element (generation of radiograph) in a predetermined cycle.

Hereinafter, each radiograph forming a dynamic image generated by dynamic-image radiography is sometimes referred to as a fame image.

[Console]

Figure 4:
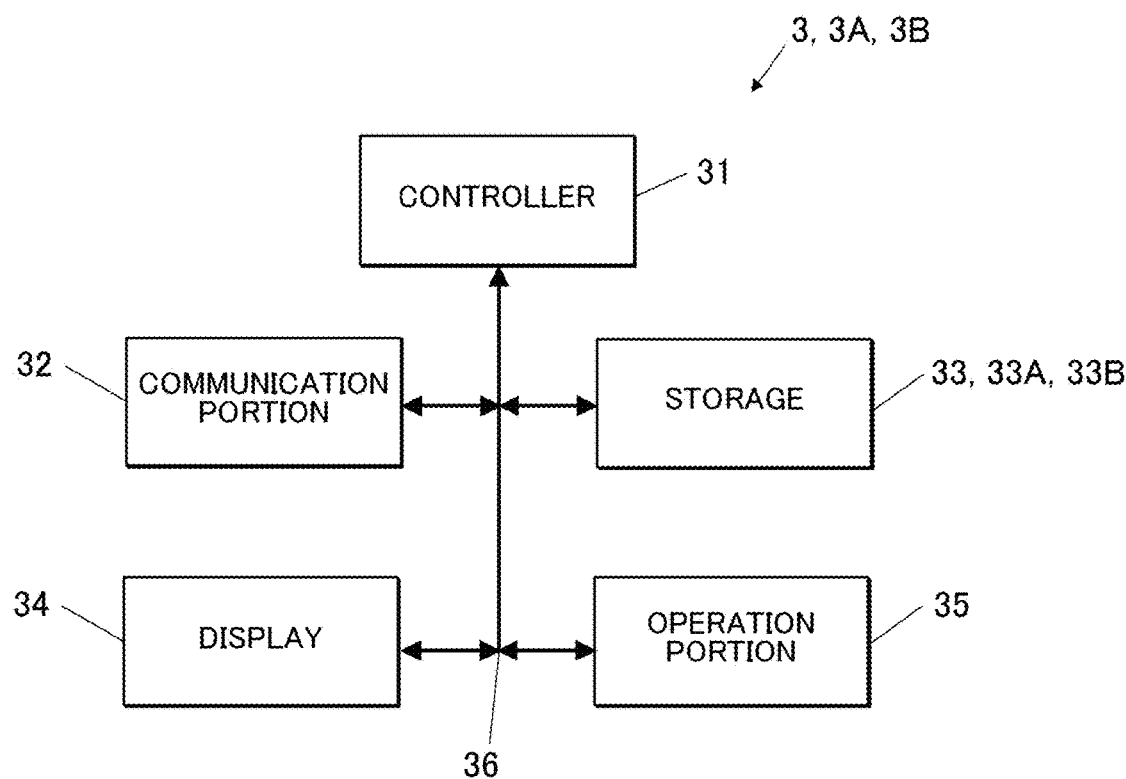
FIG. 4 is a block diagram showing a configuration of a console included in the radiographic imaging system of the first embodiment.

Next, details of the console 3 included in the above system 100 will be described. FIG. 4 is a block diagram showing a configuration of the console 3. Note that the bracketed reference numerals in FIG. 4 are those of the later-mentioned second and third embodiments.

As shown in FIG. 4, the console 3 includes a controller 31, a communication portion 32, a storage 33, a display 34, an operation portion 35, and a bus 36 that connects the parts of the console 3.

The controller 31 includes a CPU, a RAM, and the like. The CPU reads various programs stored in the storage 33 based on a control signal from another apparatus (generating apparatus 1 or radiographing apparatus 2) or an operation of the operation portion 35 to deploy the various programs stored in the storage 33 in the RAM, executes various processing according to the deployed programs, and has centralized control over operations of parts of the console 3.

The communication portion 32 is configured of a network interface or the like.

In addition, the communication portion 32 is capable of exchanging various control signals and various types of data including radiograph data with other systems (PACS 110, HIS, RIS, and the like) or other apparatuses (generating apparatus 1 and radiographing apparatus 2).

The storage 33 is configured of a nonvolatile semiconductor memory, a hard disk, or the like.

Additionally, the storage 33 stores various programs executed by the controller 31 and parameters and the like necessary for execution of processing by the programs.

Moreover, the storage 33 can store radiograph data received from the radiographing apparatus 2.

The display 34 is configured of a monitor such as a liquid crystal display (LCD) and a cathode ray tube (CRT).

Additionally, the display 34 displays a radiograph, an input instruction from the operation portion 35, various types of data, and the like according to the instruction of a display signal input from the controller 31.

The operation portion 35 includes a keyboard including cursor keys, numeric input keys, various function keys and the like, and a pointing device such as a mouse.

In addition, the operation portion 35 outputs an instruction signal input by a key operation on the keyboard or a mouse operation to the controller 31.

Moreover, the operation portion 35 may have a touch panel on the display screen of the display 34, and in this case, outputs an instruction signal input through the touch panel to the controller 31.

The controller 31 of the console of the embodiment configured in the above manner has a function of setting a radiographing condition (e.g., radiography method such as still-image radiography and dynamic-image radiography, radiographing target portion, condition regarding subject such as physique, tube voltage and tube current, irradiation time, current-time product (mAs value), frame rate (fps), and condition regarding irradiation of radiation such as expected radiographing amount or scheduled radiographing period) based on a radiographing order acquired from another system (such as RIS) or an operation of the operation portion 35 by the user.

Additionally, the controller 31 has a function of acquiring radiograph data from the radiographing apparatus 2 through the communication portion 32.

In the embodiment, in the case of dynamic-image radiography, a plurality of pieces of frame image data generated by the radiographing apparatus 2 are sequentially acquired as soon as they are transferred by the radiographing apparatus 2.

In addition, the controller 31 has a function of outputting acquired radiographs from an output portion.

In a case where the communication portion 32 serves as the output portion, the radiograph data is transmitted to another system (PACS 110, analytic diagnosis WS 120, or the like) through the communication portion 32.

Meanwhile, in a case where the display 34 serves as the output portion, the radiograph is displayed on the display 34.

Additionally, the controller 31 has a function of determining whether there is an anomaly that occurred during radiography of acquired radiographs.

In the case of dynamic-image radiography, a plurality of frame images are acquired sequentially, and therefore the determination is repeated for every acquisition of the frame image.

In the embodiment, the following determination (1) or (2) is made as to whether there is an anomaly.

(1) Determine whether there is irradiation failure or dose insufficiency based on a pixel value of a predetermined pixel in a frame image.

(2) Determine whether there is body movement of the subject based on a frame image.

When making the determination (1), it is determined that there is irradiation failure or dose insufficiency if the pixel value is less than a predetermined value, and that there is no irradiation failure or dose insufficiency if the pixel value is equal to or more than the predetermined value, for example.

The pixel to extract the pixel value used for determination may be a single pixel selected from the center of the frame, or may be pixels each selected from a plurality of areas (e.g., four areas that are upper right, upper left, lower right, and lower left of the frame) of the frame.

Instead, a plurality of pixels forming a row or a column of the frame may be selected, or a plurality of pixels covering a plurality of rows and columns of the frame may be selected.

When selecting a plurality of pixels, it is preferable that a mean value or median of pixel values of each pixel be used for the determination.

In the determination (2), it is determined that there is body movement if the amount of movement of a specific portion of the subject in a frame image is equal to or more than a predetermined value or the outline of the subject in a frame image reaches the edge of the frame image, and it is determined that there is no body movement if it is determined that the amount of movement of the specific portion is less than the predetermined value or the outline does not reach the edge of the frame image.

Additionally, on determining that there is an anomaly, the controller 31 has a function of performing an anomaly operation.

In the embodiment, as the anomaly operation, the generating apparatus 1 stops performing control for irradiating the radiographing apparatus 2 with radiation. Specifically, the operation of repeatedly turning ON the accumulation ready signal by the radiographing apparatus 2 is stopped (kept OFF).

Note that as the anomaly operation, the generating apparatus 1 may omit the operation of turning ON the irradiation instruction signal even when the second step of the exposure switch is operated.

[Flow of Radiography]

Next, a flow of dynamic-image radiography using the above system 100 will be described. FIG. 5 is a timing chart showing operations of the generating apparatus 1 and the radiographing apparatus 2 when dynamic-image radiography is performed using the system 100, and FIG. 6 is a flowchart showing an operation of the console 3 when dynamic-image radiography is performed using the system 100.

First, the user prepares for radiography. Specifically, the user arranges the subject, and sets the radiographing condition (e.g., selection of dynamic-image radiography, and input of tube voltage and tube current, frame rate, and expected radiographing amount or scheduled radiographing period for dynamic-image radiography).

After completing preparation of radiography, the user operates the first step of the exposure switch 12 of the generating apparatus 1. Then, as shown in FIG. 5, the generating apparatus 1 turns ON the irradiation preparation signal output to the radiographing apparatus 2 ($t1$).

Thereafter, the user operates the second step of the exposure switch 12. Then, the generating apparatus 1 turns ON the irradiation instruction signal output to the radiographing apparatus 2 ($t2$).

When the irradiation instruction signal is turned ON, the radiographing apparatus 2 turns ON the accumulation ready signal output to the generating apparatus 1($t3$).

In addition, at this time, the radiographing apparatus 2 turns OFF the switching element and makes the radiation detecting element ready to accumulate electrical charge.

Thereafter, the generating apparatus 1 irradiates the radiographing apparatus with radiation (t4). Then, the radiographing apparatus 2 accumulates electrical charge corresponding to the irradiated radiation in each radiation detecting element.

Thereafter, the radiographing apparatus 2 turns OFF the accumulation ready signal output to the generating apparatus 1 ($t5$). Then, the radiographing apparatus 2 reads the electrical charge accumulated in each radiation detecting element and generates a frame image. Then, the radiographing apparatus 2 transfers the frame image to the console 3.

Thereafter, as shown in FIG. 6, the console 3 acquires the frame image (step S1), and determines whether there is an anomaly that occurred during radiography of the frame image (step S2). Here, if the console 3 determines that there is no anomaly (step S2; No), the processing returns to step S1 until it is determined that the frame number of the determination target frame image is equal to the expected radiographing amount (step S3; Yes).

Meanwhile, in step S2, if the console 3 determines that there is an anomaly (step S2; Yes), the operation of turning ON the accumulation ready signal by the radiographing apparatus 2 is stopped (step S4), and a dynamic image formed of the acquired frame images is output (step S5). Then, the generating apparatus 1 is notified of the suspension of radiation irradiation.

When the console 3 performs the above control, unless an anomaly is detected in a previous frame, the turning ON of the accumulation ready signal by the radiographing apparatus 2 ($t6$, $t9$, $t12$, ... ), radiation irradiation by the generating apparatus 1 ($t7$, $t10$, $t13$, ... ), and generation of a frame image by the radiographing apparatus 2 are repeated as shown in FIG. 5 until frame images of the expected radiographing amount are generated.

Meanwhile, if an anomaly is detected in a previous frame, the generating apparatus 1 and the radiographing apparatus 2 immediately stop the operations following thereafter.

Thereafter, the user cancels the second operation of the exposure switch 12 of the generating apparatus 1. Then, as shown in FIG. 5, the generating apparatus 1 turns OFF the irradiation instruction signal output to the radiographing apparatus 2 ($t15$).

Thereafter, the user cancels the first operation of the exposure switch 12. Then, the generating apparatus 1 turns OFF the irradiation preparation signal output to the radiographing apparatus 2 ($t16$).

As has been described, the console 3 included in the system 100 of the embodiment acquires a plurality of radiographs from the radiographing apparatus 2 that repeatedly generates frame images in a predetermined cycle, determines whether there is an anomaly that occurred during radiography of the acquired radiographs, and on determining that there is an anomaly, causes the generating apparatus 1 to stop performing control for irradiating the radiographing apparatus 2 with radiation.

In conventional techniques, after completing radiography of expected radiographing amount, the dynamic image is analyzed, and the user checks the result to determine whether there is an anomaly. Hence, in a case where the radiographing is unsuccessful and needs to be performed again, the dose of radiation that the subject is exposed to until completion of the next radiography is double the case where the radiographing is completed without failure. However, in radiographing using the radiographic imaging system 100 of the embodiment, when the irradiation permission is stopped, radiographing is ended immediately. Hence, even in a case where radiographing is performed again, the dose of radiation that the subject is exposed to until completion of this radiography is reduced by a dose necessary for radiographing the number of frames obtained by subtracting the number of radiographs at the time of stoppage of the radiography from the expected radiographing amount.

Hence, in dynamic-image radiography, the exposure amount of a subject upon occurrence of an anomaly can be suppressed as compared to conventional techniques.

Additionally, since analysis requires a long time (such as several tens of minutes), the subject tends to be far away from the radiographing location by the time it is determined whether to perform radiographing again. Hence, when radiographing is actually required, the subject needs to move back to the radiographing location, which becomes a large burden on the subject.

However, in radiography using the system 100 of the embodiment, the subject can determine whether radiographing needs to be performed again, whereby such increase in the subject's burden can be prevented.

<Second Embodiment>

Next, a second embodiment of the present invention will be described. Here, configurations similar to those of the first embodiment are assigned the same reference numerals, and descriptions thereof will be omitted.

A radiographic imaging system (hereinafter referred to as system 100A) of the embodiment differs from the system 100 of the first embodiment in the operation of a console 3A.

That is, the console 3A of the embodiment differs from that of the first embodiment in processing executed by a controller 31 (program stored in storage 33A).

Note that configurations other than the console 3A are similar to the first embodiment.

Specifically, as similar to the case of the first embodiment, on determining that there is an anomaly, the controller 31 of the console 3A performs a predetermined anomaly operation.

However, in the embodiment, the following (1) or (2) is performed as the anomaly operation.

(1) Prevent an output portion from outputting a frame image generated at a timing when it is determined that there is an anomaly.

(2) Eliminate a frame image generated at a timing when it is determined that there is an anomaly.

Note that other processing that is executed by the controller 31 is similar to the first embodiment.

That is, in the embodiment, as shown in FIG. 7, in step S2 after step S1, if the console 3A determines that there is an anomaly (step S2; Yes), the processing of eliminating the frame image or preventing output of the frame image by the output portion (step S4A) is performed before performing the processing of step S3 (determination on whether frame number of determination target frame image is equal to expected radiographing amount).

When the console 3A performs such control, turning ON of the accumulation ready signal by a radiographing apparatus 2 ($t6$, $t9$, $t12$, . . . ), radiation irradiation by a generating apparatus 1 ($t7$, $t10$, $t13$, . . . ), and generation of a frame image by the radiographing apparatus 2 are repeated until frame images of the expected radiographing amount are generated regardless of whether or not an anomaly is detected. However, the frame image determined to have an anomaly is not displayed as the dynamic image.

Note that the console 3A may include a function of analyzing an acquired radiograph.

In this case, as an anomaly operation in a case where it is determined that there is an anomaly, it is also possible to perform an operation of omitting analysis of a radiograph generated at a timing when it is determined that there is an anomaly.

Additionally, in the embodiment, since it is only necessary that elimination or the like of the frame image be performed before transfer of the dynamic image to an analytic diagnosis WS 120, the acquisition of frame image and determination of whether there is an anomaly do not necessarily have to be performed immediately after transfer of the frame image by the radiographing apparatus 2 as in the above first embodiment. Instead, these operations may be performed after a certain time period.

As has been described, the console 3A included in the system 100A of the embodiment acquires a plurality of radiographs from the radiographing apparatus 2 that repeatedly generates frame images in a predetermined cycle, determines whether there is an anomaly that occurred during radiography of the acquired radiographs, and on determining that there is an anomaly, eliminates the frame image generated at the timing when it is determined that there is an anomaly or prevents output of the frame image by the output portion.

There has been a problem that when an image resulting from irradiation failure or low-dose irradiation is included in a radiographed dynamic image, analysis becomes difficult, or even if analysis is carried out, accuracy thereof is deteriorated.

However, in radiographing using the radiographic imaging system 100A of the embodiment, only images resulting from irradiation failure and low-dose irradiation are omitted from the obtained dynamic image, so that analysis can be carried out correctly by using the remaining frames. As a result, radiographing does not have to be repeated.

Hence, as similar to the case of the first embodiment, in dynamic-image radiography, the exposure amount of a subject upon occurrence of an anomaly can be suppressed as compared to conventional techniques.

<Third Embodiment>

Next, a third embodiment of the present invention will be described. Here, configurations similar to those of the first embodiment are assigned the same reference numerals, and descriptions thereof will be omitted.

A radiographic imaging system (hereinafter referred to as system 100B) of the embodiment differs from the system 100 of the first embodiment in the operation of a console 3B.

That is, the console 3B of the embodiment differs from that of the first embodiment in processing executed by a controller 31 (program stored in storage 33B).

Note that configurations other than the console 3B are similar to the first embodiment.

Specifically, the controller 31 has a function of monitoring whether there is a radiation irradiation instruction given to a generating apparatus 1 by the user.

Specifically, the controller 31 monitors whether an irradiation instruction signal input to a radiographing apparatus 2 by the generating apparatus 1 is turned ON.

Additionally, as similar to the case of the first embodiment, on determining that there is an anomaly, the controller 31 performs a predetermined anomaly operation.

Moreover, as similar to the case of the first embodiment, the controller 31 determines whether there is an anomaly that occurred during radiographing of a radiograph for every acquisition of a radiograph. However, in the embodiment, as to whether there is an anomaly is determined according to whether a radiographing instruction by the user is suspended, based on whether the timing of suspension of the irradiation instruction is earlier than when the amount of already captured radiographs reaches the expected radiographing amount, or whether the time elapsed from the start of radiographing is shorter than a scheduled radiographing period.

Additionally, as similar to the case of the first embodiment, on determining that there is an anomaly, the controller 31 performs a predetermined anomaly operation. However, in the embodiment, as the anomaly operation, the controller 31 eliminates the radiograph acquired last.

Note that other processing that is executed by the controller 31 is similar to the first embodiment.

That is, in the embodiment, as shown in FIG. 8, processing of step S3 (determination on whether frame number of determination target frame image is equal to expected radiographing amount) is performed after step S1. Here, if the console 3B determines that the frame number of the determination target frame image is not equal to the expected radiographing amount (frame number is smaller than expected radiographing amount) (step S3; No), it is determined whether the irradiation instruction signal output to the radiographing apparatus 2 by the generating apparatus 1 is turned ON (step S2A). Here, if it is determined that the irradiation instruction signal is not turned ON (step S2A; No), the frame radiographed last is eliminated (step S4B).

When the console 3B performs such control, in a case where the operation of the second step of the exposure switch is cancelled during radiography, the frame image determined that there is an anomaly, that is, radiographed last is not displayed as the dynamic image.

As has been described, the console 3B included in the system 100B sets an expected radiographing amount or a scheduled radiographing period in the generating apparatus 1, monitors whether there is a radiation irradiation instruction given to the generating apparatus 1 by the user, and determines whether a radiographing instruction by the user is suspended, based on whether the timing of suspension of the irradiation instruction is earlier than when the amount of already radiographed frame images reaches the expected radiographing amount, or whether the time elapsed from the start of radiographing is shorter than a scheduled radiographing period.

There is a case where the user accidentally releases the exposure switch 12 during radiography, and the last frame of the a plurality of radiographed frames is an image resulting from irradiation failure or low-dose exposure. There has been a problem that when such an image is included, analysis becomes difficult, or even if analysis is carried out, accuracy thereof is deteriorated.

However, in radiographing using the radiographic imaging system 100B of the embodiment, the last frame that is highly likely to be an image resulting from irradiation failure or low-dose exposure is omitted from the obtained dynamic image, so that analysis can be carried out correctly by using the remaining frames. As a result, radiographing does not have to be repeated.

Hence, as similar to the cases of the first and second embodiments, in dynamic-image radiography, the exposure amount of a subject upon occurrence of an anomaly can be suppressed as compared to conventional techniques.

<Fourth Embodiment>

Next, a fourth embodiment of the present invention will be described. Here, configurations similar to those of the first embodiment are assigned the same reference numerals, and descriptions thereof will be omitted.

While in the system 100 of the first embodiment the console 3 serves as the radiography control apparatus of the present invention, in a radiographic imaging system (hereinafter referred to as system 100C) of the embodiment, a console 3C does not have the function of the radiography control apparatus, but a radiographic imaging apparatus (hereinafter referred to as radiographing apparatus 2A) has the function instead.

That is, the radiographing apparatus 2A of the embodiment differs from the first embodiment in processing executed by a radiographing-side controller 21 (program stored in radiographing-side storage 25A).

Specifically, every time a reader 23 reads electrical charge, the radiographing-side controller 21 of the radiographing apparatus 2A determines whether an anomaly occurred when the read electrical charge was accumulated in a radiation detecting element.

Additionally, on determining that there is an anomaly, the radiographing-side controller 21 performs a predetermined anomaly operation.

Specifically, the radiographing-side controller 21 itself (radiographing apparatus 2A) performs, or causes a generating apparatus 1 or the console 3C to perform any of the anomaly operations described in the above one to third embodiments.

Note that in a case such as this embodiment where the radiographing apparatus 2A determines whether there is an anomaly, it is possible to determine whether there is an anomaly before generating a frame image. Hence, on determining that there is an anomaly, it is possible to prevent generation of a radiograph based on the electric charge accumulated at the timing when it is determined that there is an anomaly, for example.

Additionally, with the image generation function of the radiographing apparatus 2A, a frame image before or after the frame image determined to have an anomaly may be used for interpolation.

As has been described, the radiographing apparatus 2A included in the system 100C of the embodiment includes a radiation detector 22 in which a plurality of radiation detecting elements that generate electrical charge corresponding to the received dose of radiation are arranged in a two-dimensional manner, alternates accumulation of electrical charge in the radiation detecting elements and reading of the electrical charge accumulated in the radiation detecting elements repeatedly in a predetermined cycle, determines whether an anomaly occurred when the read electrical charge was accumulated in the radiation detecting element, and on determining that there is an anomaly, performs any of the anomaly operations described in the above first to third embodiments.

Hence, as similar to the cases of the first to third embodiments, in dynamic-image radiography, the exposure amount of a subject upon occurrence of an anomaly can be suppressed as compared to conventional techniques.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-181247, filed on 27th of September, 2018, is incorporated herein by reference in its entirety.

What is claimed is:

1. A radiography control apparatus comprising:
   a hardware processor that:
      acquires a plurality of radiographs from a radiographic imaging apparatus when the radiographic imaging apparatus performs dynamic-image radiography by radiation to capture motion within a subject;
      determines whether there is an anomaly that occurred during the dynamic- image radiography; and
      on determining that there is an anomaly, performs a predetermined anomaly operation; and
   an output portion that outputs the plurality of radiographs.

2. The radiography control apparatus according to claim 1, wherein the output portion outputs a dynamic image including the plurality of radiographs.

3. The radiography control apparatus according to claim 2, wherein:
   the output portion includes a transmitter that transmits the dynamic image, and the transmitter transmits the dynamic image to an analytical diagnosis workstation in which analysis is performed based on the dynamic image.

4. The radiography control apparatus according to claim 2, wherein the output portion includes a display that displays the dynamic image.

5. The radiography control apparatus according to claim 2, wherein on determining that there is an anomaly, the hardware processor:
   stops control of irradiating the radiation by a radiation generating apparatus that irradiates the radiation, and
   controls the output portion to output the dynamic image including the plurality of radiographs acquired up to a point at which it is determined that there is an anomaly.

6. The radiography control apparatus according to claim 1, wherein the hardware processor determines whether there is irradiation failure or dose insufficiency based on the acquired radiographs.

7. The radiography control apparatus according to claim 6, wherein the hardware processor determines whether there is irradiation failure or dose insufficiency based on a pixel value of a predetermined pixel in the acquired radiographs.

8. The radiography control apparatus according to claim 1, wherein the hardware processor determines whether there is body movement of the subject based on the acquired radiographs.

9. The radiography control apparatus according to claim 1, wherein on determining that there is an anomaly, the hardware processor eliminates a radiograph generated at a timing at which it is determined that there is an anomaly.

10. The radiography control apparatus according to claim 1, wherein on determining that there is an anomaly, the hardware processor prevents the output portion from outputting a radiograph generated at a timing at which it is determined that there is an anomaly.

11. The radiography control apparatus according to claim 1, wherein the hardware processor:
  analyzes the acquired radiographs; and
  on determining that there is an anomaly, does not analyze a radiograph generated at a timing at which it is determined that there is an anomaly.

12. The radiography control apparatus according to claim 1, wherein the hardware processor:
  is configured to set an expected radiographing amount or a scheduled radiographing period in a radiation generating apparatus that irradiates the radiation;
  monitors whether there is a radiation irradiation instruction given to the radiation generating apparatus by a user; and
  determines whether a radiographing instruction by the user is suspended, based on whether a timing of suspension of the irradiation instruction is earlier than a timing at which an amount of already captured radiographs reaches the expected radiographing amount, or whether a time elapsed from a start of radiographing is shorter than the scheduled radiographing period.

13. The radiography control apparatus according to claim 12, wherein on determining that there is an anomaly, the hardware processor eliminates a most recently acquired radiograph.

14. A radiographic imaging system comprising:
  the radiography control apparatus according to claim 1; and
  the radiographic imaging apparatus that repeatedly generates the radiographs in a predetermined cycle.

15. A radiographic imaging apparatus comprising:
  a radiation detector in which a plurality of radiation detecting elements that generate electrical charge corresponding to a received dose of radiation are arranged in a two-dimensional manner; and
  a hardware processor that:
    alternates accumulation of electrical charge in the radiation detecting elements and reading of the electrical charge accumulated in the radiation detecting elements repeatedly in a predetermined cycle when dynamic-image radiography by radiation is performed to acquire radiographs capturing motion within a subject;
    determines whether an anomaly occurred when the electrical charge was accumulated in the radiation detecting elements; and
    on determining that there is an anomaly, performs a predetermined anomaly operation.

16. A radiographic imaging system comprising the radiographic imaging apparatus according to claim 15.

17. A non-transitory computer-readable storage medium storing a program executable by a computer to cause the computer to perform control of processes comprising:
  a first process in which a plurality of radiographs are acquired from a radiographic imaging apparatus when the radiographic imaging apparatus performs dynamic-image radiography by radiation to capture motion within a subject;
  a second process in which it is determined whether there is an anomaly that occurred during the dynamic-image radiography;
  on determining that there is an anomaly in the second process, a third process in which a predetermined anomaly operation is performed; and
  a radiograph output process in which the plurality of radiographs are output from an output portion.

18. The non-transitory computer-readable storage medium according to claim 17, wherein in the radiograph output process, the output portion outputs a dynamic image including the plurality of radiographs.

19. The non-transitory computer-readable storage medium according to claim 18, wherein:
  the output portion includes a transmitter that transmits the dynamic image, and
  the transmitter transmits the dynamic image to an analytical diagnosis workstation in which analysis is performed based on the dynamic image.

20. The non-transitory computer-readable storage medium according to claim 18, wherein the output portion includes a display that displays the dynamic image.

21. The non-transitory computer-readable storage medium according to claim 18, further comprising, on determining that there is an anomaly in the second process, stopping control of irradiating the radiation by a radiation generating apparatus that irradiates the radiation, and controlling the output portion to output the dynamic image including the plurality of radiographs acquired up to a point at which it is determined that there is an anomaly.

* * * * *